(12) United States Patent
Ascani

(10) Patent No.: US 8,020,389 B2
(45) Date of Patent: Sep. 20, 2011

(54) ENERGY-SAVING CLIMATIC TEST CHAMBER AND METHOD OF OPERATION

(75) Inventor: Maurizio Ascani, Perugia (IT)

(73) Assignee: Angelantoni Industrie SpA, Massa Martana (IT)

( * ) Notice: Subject to any disclaimer, the term of this patent is extended or adjusted under 35 U.S.C. 154(b) by 1108 days.

(21) Appl. No.: 11/722,092

(22) PCT Filed: Dec. 20, 2004

(86) PCT No.: PCT/IT2004/000710
§ 371 (c)(1),
(2), (4) Date: Jun. 19, 2007

(87) PCT Pub. No.: WO2006/067810
PCT Pub. Date: Jun. 29, 2006

(65) Prior Publication Data
US 2009/0205344 A1 Aug. 20, 2009

(51) Int. Cl.
*F25B 41/00* (2006.01)
*F25B 49/00* (2006.01)
*F25B 1/00* (2006.01)
*F25B 7/00* (2006.01)
*F25D 17/02* (2006.01)

(52) U.S. Cl. ............. 62/113; 62/185; 62/201; 62/228.5; 62/335; 62/434

(58) Field of Classification Search .............. 62/201, 62/185, 197, 113, 513, 434; 374/29, 141, 374/147, 109; 73/863.11, 116.02
See application file for complete search history.

(56) References Cited

U.S. PATENT DOCUMENTS

| 3,656,540 | A | * | 4/1972 | Henrici | 62/498 |
| 3,808,827 | A | * | 5/1974 | Avon et al. | 62/59 |
| 4,027,495 | A | * | 6/1977 | Edwards | 62/48.2 |
| 4,406,138 | A | * | 9/1983 | Nelson | 62/305 |
| 4,696,168 | A | * | 9/1987 | Woods et al. | 62/200 |
| 4,720,981 | A | | 1/1988 | Helt et al. | |
| 4,798,059 | A | | 1/1989 | Morita et al. | |
| 4,840,037 | A | * | 6/1989 | Yamada et al. | 62/199 |
| 4,964,279 | A | * | 10/1990 | Osborne | 62/59 |
| 5,372,011 | A | * | 12/1994 | O'Neal | 62/93 |
| 5,647,225 | A | * | 7/1997 | Fischer et al. | 62/434 |
| 5,924,307 | A | * | 7/1999 | Nenov | 62/643 |
| 6,434,960 | B1 | | 8/2002 | Rousseau | |
| 6,543,245 | B1 | * | 4/2003 | Waldschmidt et al. | 62/239 |
| 6,993,923 | B2 | * | 2/2006 | Beers | 62/228.1 |

FOREIGN PATENT DOCUMENTS

EP  1 452 808 A  9/2004
* cited by examiner

*Primary Examiner* — Frantz F Jules
*Assistant Examiner* — Filip Zec
(74) *Attorney, Agent, or Firm* — Fredrikson & Byron, P.A.

(57) ABSTRACT

Climatic test chamber (10) for carrying out a sequence of specified test cycles and cooled by means of at least a refrigerating circuit (100, 200, 410) including a variable-speed compressor (120, 210, 410). During the steps of the test cycles in which said chamber (10) is held at a minimum set temperature, the compressor (120, 210, 410) operates at the minimum rotating speed thereof and the refrigeration capacity is used to cool a cold storage medium. The cold stored by the cold storage medium is then recovered to subcool the refrigerant medium during the cooling-down steps in which the compressor (120, 210, 410) operates at the maximum rotating speed thereof.

17 Claims, 2 Drawing Sheets

ENERGY-SAVING CLIMATIC TEST CHAMBER AND METHOD OF OPERATION

Figure 1:
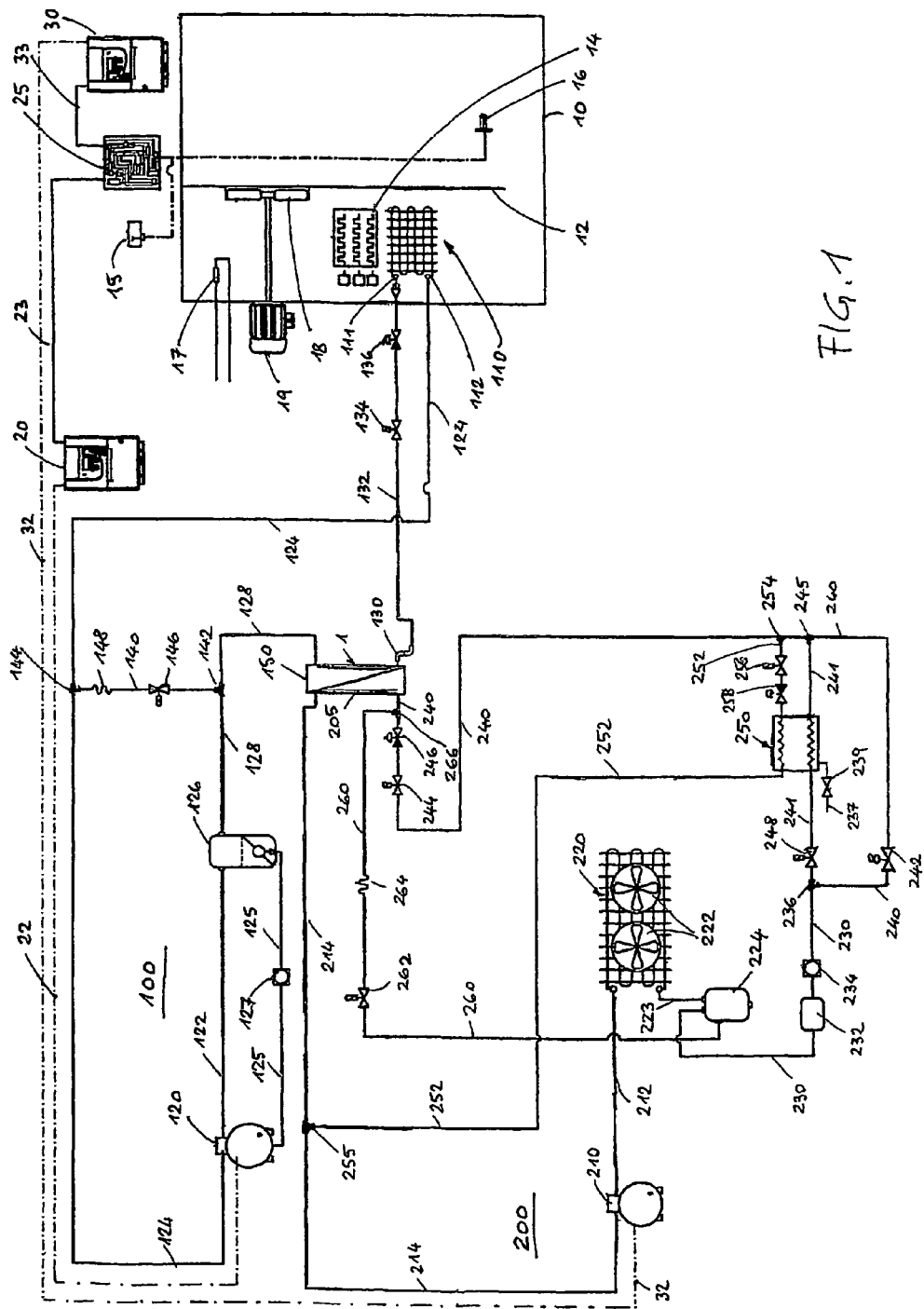

The present invention refers to climatic test chambers of the kid used in testing laboratories to submit specimens of materials and/or components, duly loaded and arranged in thermally insulated cavities, to specified numbers of temperature cycles.

These temperature cycles consist of heating-up steps alternating with cooling-down steps, with periods of a pre-set length of time provided therebetween, in which said specimens are held at a maximum temperature and a minimum temperature, wherein the temperature values involved are in each case provided for by the test specifications relating to the materials and/or components being tested.

While no particular problems are encountered in being capable of reaching and maintaining a maximum temperature, although the latter may also reach up to +180° C., since using conventional electric heating elements having a higher or lower power rating is all that it required to such purpose, reaching down to the minimum required temperature, which of course implies the use of a refrigerating unit, meets with a number of problems, especially when this minimum temperature has a very low value, e.g. −70° C.

A first problem connected with the use of a refrigerating unit relates to the kind of equipment that is actually needed. A solution to this problem, while altogether easy from a mere technical point of view, is anyway quite expensive. In order to be able to reach down to minimum temperatures having such low values, the refrigerating unit must in fact be of the two-stage cascade type, in which the evaporator of the higher-temperature stage or circuit is arranged in a heat-exchange condition with the condenser of the lower-temperature stage or circuit. It is therefore the evaporator of the lower-temperature stage (in which use is made of a refrigerant medium having a lower boiling point than the refrigerant medium used in the higher-temperature stage) that is physically in a heat-exchange condition with the heat-insulated cavity of the climatic test chamber.

A second and, for the matter, much more serious problem derives from the fact that, owing to the cool-down rate (i.e. the time taken to bring the interior of the heat-insulated cavity from its maximum temperature down to its minimum temperature) being actually a quite critical factor, the refrigerating capacity to be provided by the refrigerating unit to maintain the minimum set temperature fox the required length of time, turns out to make up just quite a modest percentage (approximately 10%) of the refrigeration capacity to be provided during the cooling-down steps. Since such minimum temperature must be maintained within very tight tolerances, typically amounting to ±0.5° C., it is not possible to make use of a repeated, frequent ON/OFF cycling of the compressors in the stages or circuits of the refrigerating unit, being it on the contrary necessary for these compressors to be kept continuously operating, albeit under an appropriate utilization of adjustable flow-rate solenoid valves.

The generally adopted prior-art solution to this second problem lies in providing and activating appropriate by-pass arrangements so as to cut off the flow of the refrigerant media in the evaporator of the higher-temperature stage, as well as in the condenser, the expansion valve and the evaporator of the lower-temperature stage. In this manner, the refrigerant media keep circulating between the delivery side and the suction side of the respective compressors. Anyway, quite apparent is the considerable amount of energy that is wasted in this way, considering also the fact that the flow rate of the refrigerant media remains unaltered, i.e. remains the same both during the cool-down steps and while the cavity is maintained at its minimum set temperature.

It would on the contrary be desirable, and is actually a main object of the present invention, to prevent such considerable amount of energy from being wasted while the heat-insulated cavities of the climatic test chamber are being held at the minimum set temperature.

A further object of the present invention is to increase the cool-down rate of the climatic test chambers, so that the duration of the cool-down steps and, as a result, of the temperature cycles is decreased accordingly, with a clear advantage for the customers of the laboratory test facilities, even from a cost standpoint thanks to the lower energy consumption implied.

According to the present invention, these objects, along with further ones that will become apparent from the following description, are reached in climatic test chambers incorporating the features and characteristics as recited in the appended claims.

Figure 2:
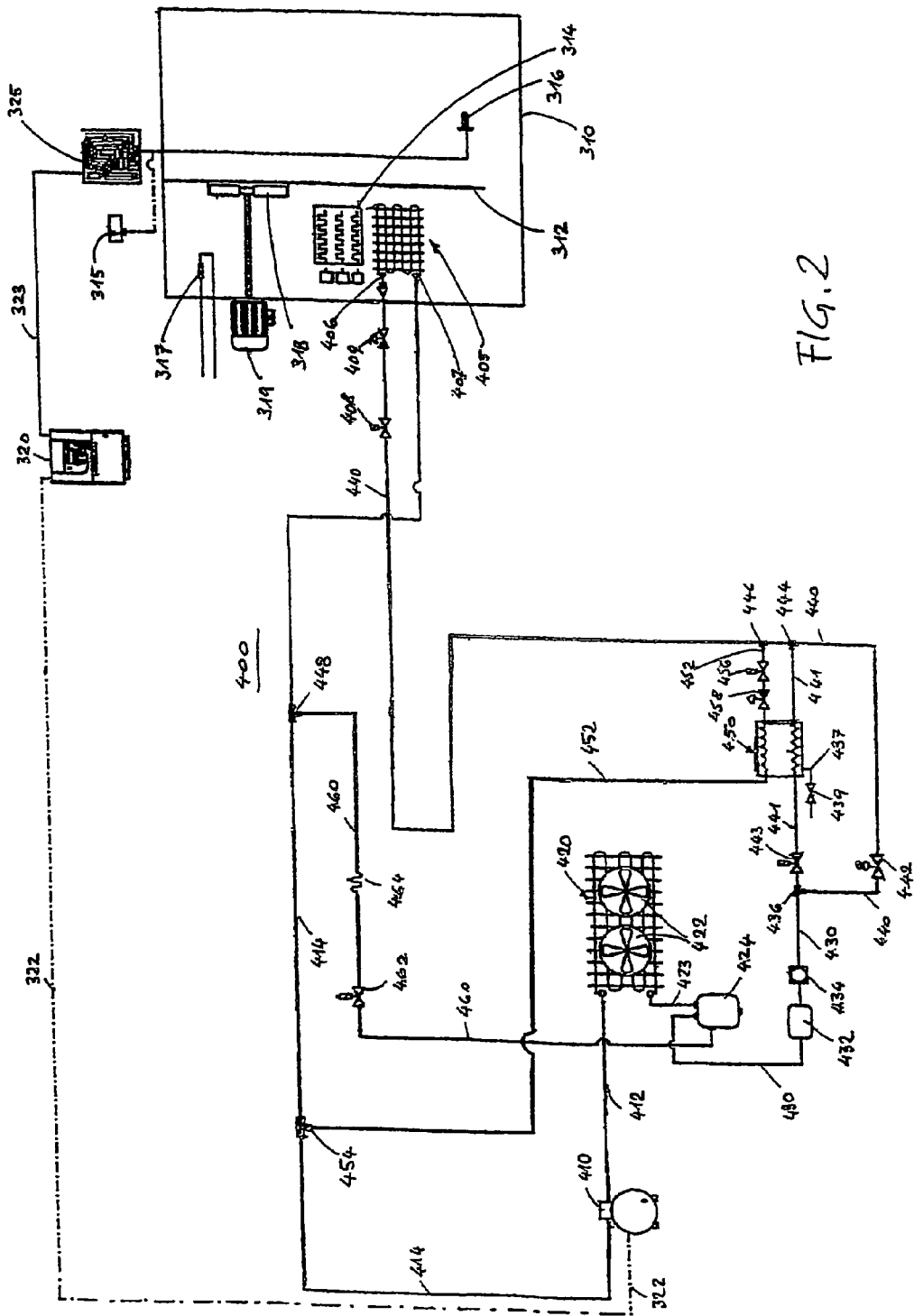

Features and characteristics of the inventive climatic test chambers, as well as the advantages thereof over prior-art solutions will anyway be more readily understood from the description that is given below of a couple of preferred, although not sole embodiments. Considering that all of the herein characteristics claimed herein refer to the refrigerating unit of the climatic test chambers, in the accompanying drawing:

FIG. 1 illustrates the circuit diagram of a two-stage cascade refrigerating unit according to the present invention, where all generally known parts and items that must be used to comply the requirements and provisions of safety standard regulations and/or to carry out auxiliary operations (filling of refrigerant media, maintenance, and the like), but have no relevance at all as far as the present invention is concerned, have been intentionally omitted for a better clarity; and FIG. 2 illustrates a similar circuit diagram for a single-stage refrigerating unit.

The fluid-dynamic circuit of the lower-temperature stage, which is generally indicated at 100 in FIG. 1 and may for example use R23 (i.e. methyl trifluoride) as a refrigerant medium, comprises the following components:

an evaporator 110, consisting of a battery of finned pipes arranged inside the heat-insulated cavity 10 of the climatic test chamber, behind a baffle plate 12 provided to divert the flow of air. In a per se known manner, inside the cavity 10 there are also provided a group of electric heating elements 14 (actually, a group of sheathed resistance-type heating elements in a parallel-connected arrangement), the probe 16 of an adjustable thermostat 15 for setting and controlling a highest temperature and a lowest set temperature, a temperature-limiting safety thermostat 17, the impeller 18 of a motor-driven fan 19 adapted to provide a regular flow of air inside the cavity 10. The adjustable thermostat 15 is arranged outside the cavity 10 and is associated to a PLC 25 controlling the entire climatic test chamber. In particular, the PLC 25 is connected, via respective electric connections 23 and 33, with two inverters 20 and 30 and is energized from the power-supply mans. The temperature-limiting safety thermostat 17 is in turn connected to the conventional lines (not shown, but connected to the power-supply mains) for energizing the electric heating elements 14;

a compressor 120 (referred to as the "first compressor" hereinafter) driven by an asynchronous motor, connected via the power line 22 to the inverter 20 that controls the rotating speed thereof between a maximum and a minimum set value;

the delivery pipe 122 of the compressor 120, on which there is provided an oil separator 126 connected with the lower base of the compressor via a service pipe 125 (running parallel to the same delivery pipe 122), where an oil-flow indicator 127 is installed for indicating the passage of oil;

a pipe 128 connecting the oil separator 126 with the condenser 105, which forms the hot side of a counter-flow heat exchanger 150;

a reservoir 130 for collecting the liquid refrigerant medium, placed at the end of the pipe 128, which is connected to the inlet 111 of the evaporator 110 via a pipe 132 on which there are provided in sequence a solenoid valve 134 (hereinafter referred to as solenoid valve I) and a thermostatically controlled valve 136 forming the throttling member of the circuit 100 of the lower-temperature stage;

the return or suction pipe 124 of the compressor 120, which has a larger diameter than the delivery pipe 122 and is connected to the outlet 112 of the evaporator 110.

In this first embodiment of the present invention, the fluid-dynamic circuit 100 of the lower-temperature stage finally comprises a by-pass line 140 connected to the delivery pipe 122 of the first compressor 120 via a T-fitting 142 (hereinafter referred to as the sixth fitting), and connected further to the suction pipe 124 of the same compressor via another T-fitting (seventh fitting). Starting from the sixth fitting 142, on the by-pass line 140 there are installed in a sequence a solenoid valve 146 (hereinafter referred to as solenoid valve II) and a capillary tube 148.

The fluid-dynamic circuit of the higher-temperature stage, which is generally indicated at 200 in FIG. 1 and may for example use R404a (i.e. a blend of 44.1% of R125, 51.9% of R143a, and 4.0% of 134a) as a refrigerant medium, in turn comprises the following components:

a compressor 210 (hereinafter referred to as the second compressor) driven by an asynchronous motor, connected via the power line 32 to the inverter 30 that controls the rotating speed thereof between a maximum and a minimum set value;

the delivery pipe 212 of the compressor 210;

the return or suction pipe 214 of the compressor 210, which has a larger diameter than the delivery pipe 212 and is connected to the outlet of the cold side of the heat exchanger 150;

a condenser 220 (actually a battery of finned tubes with the related motor-driven cooling fans), located at the end of the delivery pipe 212 of the compressor 210 and connected via a short connection pipe 223 to a reservoir 224 for the liquid refrigerant medium;

an outlet pipe 230 from the reservoir 224, on which there are provided in a sequence: a drying filter 232, an oil-flow indicator 234 for indicating the passage of oil, and a T-fitting 236 (hereinafter called first fitting). From this first fitting 236 there departs a pipe 240 (referred to as the main pipe), on which there are installed, in a sequence, the solenoid valves 242, 244 (hereinafter referred to as solenoid valve III and solenoid valve IV, respectively) and a thermostatically controlled valve 246 forming the throttling member of the fluid-dynamic circuit of the higher-temperature stage 200. The main pipe 240 reaches up to the evaporator 205 of the circuit 200 of the higher-temperature stage 200, which forms the cold side of the already mentioned heat exchanger 150.

According to a basic feature of the present invention, from said first T-fitting 236 there also departs a secondary pipe 241, in which there is installed a solenoid valve 248 (hereinafter referred to as solenoid valve V), and which extends through a sealed tank 250 to eventually end into the main pipe 240 via a T-fitting 245 (hereinafter referred to as the second fitting) situated downstream of the solenoid valve III 242. In the tank 250 (which forms another important feature of the present invention and is hereinafter referred to as storage tank, since it acts as a cold storage means, as this shall be explained in greater detail further on) there is filled, via a pipe 237 provided with a gate valve 239, a eutectic liquid of any suitable type, such as for instance an aqueous ethylene glycol solution.

Further to the secondary pipe 241, through the tank 250 there passes also a coil-shaped length of a pipe 252, which shall be referred to as the recovery pipe hereinafter. The recovery pipe 252 starts off a T-shaped fitting 254 (hereinafter referred to as the third fitting), which is situated downstream of the second fitting 245 and upstream of the solenoid valve IV 244, and provided in a sequence on the pipe 252 there also are a further solenoid valve 256 (hereinafter referred to as solenoid valve VI) and a thermostatically controlled valve 258. The recovery pipe 252 continues downstream of the storage tank 250 until it reaches its termination point at another T-shaped fitting 255 (hereinafter referred to as the fifth fitting) situated on the suction pipe 214 of the second compressor 210 downstream of the outlet of the cold side of the heat exchanger 150.

In this embodiment of the present invention, the fluid-dynamic circuit 200 of the higher-temperature stage finally comprises a by-pass line 260 that comes out of the reservoir 224 of the liquid refrigerant medium, at a separate position with respect to the pipe 230, and ends into a T-fitting 266 (hereinafter referred to as the fourth fitting) on the main pipe 240 at a location situated between the throttle valve 246 and the inlet of the cold side of the heat exchanger 150. In a per se known manner, on the by-pass line 260 there are provided in a sequence a further solenoid valve 262 (hereinafter referred to as solenoid valve VII) and a capillary tube 264.

The mode of operation is as follows, under the assumption that, for the kind of test to be performed in the climatic chamber, the specifications demand carrying out N cycles consisting sequentially of four steps, i.e.: heating up the specimen placed in the heat-insulated cavity of the chamber up to a maximum set temperature $t_1=+170°$ C.; maintaining the specimen at said temperature $t_1$ for 3 hours; cooling down the specimen to a minimum set temperature $t_2=-70°$ C.; maintaining the specimen at said temperature $t_2$ for 3 hours.

In the first one of the N test cycles to be carried out according to the specification, the operation of the apparatus is a fully traditional one, i.e. the first two steps are carried out by making use of the electric heating elements 14, as assisted by the motor-driven fan 19, under the control of the PLC 25. In the following cooling-down step, the PLC 25, upon having first switched off the heating elements 14, while however keeping the motor-driven fan 19 regularly operating, causes the inverters 20 and 30 to supply the drive motors of the compressors 120 and 210 at the maximum frequency, e.g. 60 Hz if the line frequency is 50 Hz, until the probe 16 connected to the PLC eventually detects that the temperature $t_2$ has been reached in the cavity 10. During this cooling-down step, the PLC 25 makes sure that the state of the solenoid valves in the circuits is as indicated in Table I below, wherein ON means that the solenoid of the corresponding valve is energized, while OFF means that it is de-energized.

TABLE 1

| I = 134 | II = 146 | III = 242 | IV = 244 | V = 248 | VI = 256 | VII = 262 |
|---------|----------|-----------|----------|---------|----------|-----------|
| ON | OFF | ON | ON | OFF | OFF | OFF |

It therefore ensues that both stages of the refrigerating unit operate at full capacity and need a certain time $T_1$ (which therefore is the duration of the third step of the first operating cycle) to bring down the temperature in the cavity 10 from $t_1$ to $t_2$.

In the following fourth step of the test cycle, during which the PLC 25 maintains the cavity 10 at the minimum set temperature $t_2$, the inverter 20 and the inverter 30 decrease the speed of rotation of the motors of both compressors 120 and 210. Upon so reaching the lowest speed allowed for by a correct operation of the compressors, the PLC 25 ensures that, throughout the duration of this fourth step, the state of the solenoid valves in the circuits is as indicated in Table 2 below:

TABLE 2

| I = 134 | II = 146 | III = 242 | IV = 244 | V = 248 | VI = 256 | VII = 262 |
|---------|----------|-----------|----------|---------|----------|-----------|
| ON      | OFF      | ON        | ON       | OFF     | ON       | OFF       |

As a result, considering the very small amount of refrigerating power needed by the cavity 10 in this step, it is almost the entire refrigerating capacity of the circuit 200 of the higher-temperature stage that is no longer used in the heat exchanger 150 to cool down the refrigerant medium flowing into the circuit 100 of the lower-temperature stage. According to a basic feature of the present invention, the refrigerating capacity of the circuit 200 of the higher-temperature stage 200 is rather used to cool down (to the freezing point) the eutectic liquid in the storage tank 250 via the recovery pipe 252.

In the cooling-down step of the next (second) of the N specified temperature cycles, the PLC 25 ensures that the state of the solenoid valves in the circuits is as indicated in Table 3 below:

TABLE 3

| I = 134 | II = 146 | III = 242 | IV = 244 | V = 248 | VI = 256 | VII = 262 |
|---------|----------|-----------|----------|---------|----------|-----------|
| ON      | OFF      | OFF       | ON       | ON      | ON       | OFF       | so that in the secondary pipe 241, i.e. upstream of the throttle valve 246, the refrigerant medium is subcooled by the cold accumulated in the tank 250, with readily understandable advantages from a thermodynamic point of view.

This subcooling, by affecting and conditioning the evaporation of the same refrigerant medium in the heat exchanger 150, has a favourable effect on the condensation of the refrigerant medium in the circuit 100 of the lower-temperature circuit, thereby boosting the efficiency of the latter. The ultimate result is that the duration of the third step of the second operating cycle, in which the temperature in the cavity 10 is brought down from $t_1$ to $t_2$, is not the same one as the time $T_I$ needed in the first cycle, but has a value $T_{II}$, that is considerably shorter than $T_I$. The fourth step of the second operating cycle is similar to the fourth step of the first operating cycle.

All subsequent test cycles to be performed in accordance with the specifications will then take place in the same manner and mode as above described in connection with the second cycle.

Most readily appreciable from the above description is the reduction in the overall duration of a laboratory test and, as a result, in the related energy consumption, from which there derives, for the customer that ordered the test, the clear advantage of being able to obtain the desired test results in a much shorter time, as well as pay a lower price for the test, whereas for those who run the test laboratory and use the climatic test chamber, the resulting advantage lies in the ability of running a greater number of tests in a given period of time, e.g. one year.

Should the condition occur, in which the cold storage in the tank 250 has been fully completed, i.e. the eutectic liquid loaded therein has been fully frozen, the by-pass function of the circuit 200 is activated. The PLC 25 then ensures that the state of the solenoid valves in the circuits is as indicated in Table 4 below:

TABLE 4

| I = 134 | II = 146 | III = 242 | IV = 244 | V = 248 | VI = 256 | VII = 262 |
|---------|----------|-----------|----------|---------|----------|-----------|
| ON      | OFF      | OFF       | ON       | ON      | OFF      | ON        |

Going now on to describe the second embodiment of the present invention, which is illustrated in FIG. 2 and comprises a single-stage refrigerating unit, it should first of all be noticed that such embodiment is intended for application when the minimum set temperature of the test cycles to be performed is higher than in the first embodiment, i.e. has for instance a value $t_2 = -20°$ C., whereas the value of the maximum or highest temperature may be the same as the one considered in connection with the first embodiment, i.e. $t_1 = +170°$ C.

The fluid-dynamic circuit, which is generally indicated at 400 in FIG. 2 and uses for instance R404A as a refrigerant medium, is used to cool down, with its evaporator 405, the heat-insulated cavity 310 of a climatic test chamber. Inside the cavity 310 there are arranged, further to the evaporator 405: the probe 316 of an adjustable thermostat 315 for setting and controlling a maximum and a minimum set temperature; a group of electric heating elements 314 controlled by a temperature limiting thermostat 317 behind a baffle plate 312 for deflecting the air flow; the impeller 318 of a motor-driven fan 319 adapted to provide a regular flow of air inside the cavity 310. The adjustable thermostat 315 is arranged outside the cavity 310 and is associated to a PLC 325 controlling the entire climatic test chamber. In particular, the PLC 325 is connected, via an electric line 323, with an inverter 320 and is energized from the power-supply mains. The temperature-limiting safety thermostat 317 is in turn connected to the conventional power-supply line (not shown) of the electric heating elements 314.

The circuit 400 comprises, further to the above-mentioned evaporator 405, which has an inlet 406 and an outlet 407:

a first solenoid shut-off valve 408 (hereinafter referred to as solenoid valve I) and a thermostatically controlled valve 409 forming the throttling member of the circuit, situated upstream of the inlet 406 of the evaporator 405 along a pipe 440, referred to as the main pipe hereinafter;

a compressor 410 driven by an asynchronous motor controlled by the inverter 320, to which it is connected via the power supply line 322;

the delivery pipe 412 of the compressor 410;

the return or suction pipe 414 of the compressor 410, which has a larger diameter than the delivery pipe 412 thereof and is connected to the outlet 407 of the evaporator 405;

a condenser 420 (actually a battery of finned tubes with the related motor-driven cooling fans 422), located at the end of the delivery pipe 412 of the compressor 410 and connected via a short connection pipe 423 to a reservoir 424 for the liquid refrigerant medium;

an outlet pipe 430 from the reservoir 424, on which there are provided in a sequence: a drying filter 432, an oil-flow indicator 434 for indicating the passage of oil, and a T-fitting 436 (hereinafter called first fitting). This first fitting 436 is the site where the above-mentioned main pipe 440 and a so-called secondary pipe 441 (that forms a basic feature of the present invention as this shall be explained in greater detail further on) flow into.

Along the main pipe 440, starting from the first fitting 436 upstream of the solenoid valve I 408 and the throttle valve 409, a solenoid valve 442 (solenoid valve II), a second T-fitting 444, a third T-fitting 446 and a fourth T-fitting 448 are provided in a sequence.

The secondary pipe 441 comprises in turn, downstream of a solenoid valve 443 (solenoid valve III), a coil-shaped length thereof passing through a sealed tank 450 and ends into the main pipe 440 via the second T-fitting 444, this T-fitting being situated downstream of the solenoid valve II 442, as above noted.

The tank 450 acts as a cold storage means or cold accumulator, since it is filled, via a pipe 437 provided with a gate valve 439, with a eutectic liquid of any suitable type, such as an aqueous ethylene glycol solution. Further to the secondary pipe 441, through the tank 450 there passes also a coil-shaped length of a so-called recovery pipe 452. This recovery pipe 452 branches off the main pipe 440 from the afore cited third T-shaped fitting 446 and, downstream of said coiled length thereof, it joins and flows into the return or suction pipe 414 of the compressor 410 at the site where a fifth T-fitting 454 is provided. A further solenoid valve 456 (solenoid valve T) and a further thermostatically controlled valve 458 are sequentially provided between said third T-fitting 446 and the beginning of said coiled length of the recovery pipe 452.

In a per se known manner, the circuit 400 finally comprises a by-pass line 460 that comes out of the reservoir 424 of the liquid refrigerant medium, which is located immediately downstream of the condenser 424, and flows into the return or suction pipe 414 of the compressor 410 at the site where the fourth T-fitting 448 is provided. A last valve 462 (solenoid valve V) and a capillary tube 464 are sequentially provided on the by-pass line 460.

The mode of operation is as follows, under the assumption that, for the kind of test to be performed in the heat-insulated cavity 310 of the climatic chamber, the specifications demand carrying out N cycles consisting of four steps, i.e. heating up the specimen placed in the heat-insulated cavity of the chamber up to a maximum set temperature $t_1=+170°$ C.; maintaining the specimen at the temperature $t_1$ for 3 hours; cooling down the specimen to a minimum temperature $t_2=-20°$ C.; maintaining the specimen at the temperature $t_2$ for 3 hours.

In the first two steps of the first one of the specified N test cycles, the cavity 310 is heated up by the electric heating elements 314, as assisted by the motor-driven fan 319, under the control of the PLC 325. In the following cooling-down step, the PLC 325, upon having first switched off the heating elements 314, while however keeping the motor-driven fan 419 regularly operating, causes the inverter 320 to supply the drive motor of the compressor 410 at the maximum frequency, e.g. 60 Hz if the line frequency is 50 Hz, so that the speed of rotation thereof reaches up to the highest allowable value thereof. During this third step of the first operating cycle, which is terminated upon the probe 316 of the PLC 325 indicating that the set temperature $t_2=-20°$ C. has eventually been reached inside the cavity 310 and, as a result, upon a time $T_I$ having elapsed, the PLC 325 makes sure that the state of the solenoid valves in the circuit is as indicated in Table 5 below:

TABLE 5

| $I^A = 408$ | $II^A = 442$ | $III^A = 443$ | $IV^A = 456$ | $V^A = 462$ |
|---|---|---|---|---|
| ON | ON | OFF | OFF | OFF |

This results in a generally traditional operation of the refrigerating circuit 400, which on the other hand keeps operating in a traditional manner also in the following fourth step of this first test cycle. During this fourth step, which has a pre-set duration, the inverter 320 in fact decreases the speed of rotation of the motor of the compressor 410 down to the lowest speed allowed for by a correct operation of the same compressor, and the PLC 325 ensures that the state of the solenoid valves in the circuit is as indicated in Table 6 below:

TABLE 6

| $I^A = 408$ | $II^A = 442$ | $III^A = 443$ | $IV^A = 456$ | $V^A = 462$ |
|---|---|---|---|---|
| ON | OFF | ON | ON | OFF |

As a result, given the very small amount of refrigerating capacity needed by the cavity 310 to maintain the minimum set temperature, almost the entire refrigerating capacity of the circuit 400 is at this point rather used to cool down (to the freezing point) the eutectic liquid in the cold storage tank 450 via the recovery pipe 452, in accordance with the afore cited basic feature of the present invention.

In the next operating cycle, i.e. the second of the specified N cycles, the PLC 325 ensures that, in the third step where the specimen temperature in the cavity 310 is cooled down, the state of the solenoid valves in the circuit is as indicated in Table 7 below,

TABLE 7

| $I^A = 408$ | $II^A = 442$ | $III^A = 443$ | $IV^A = 456$ | $V^A = 462$ |
|---|---|---|---|---|
| ON | OFF | ON | OFF | OFF |

With the result that in the secondary pipe 441, i.e. upstream of the throttle valve 408, the refrigerant medium is subcooled by the cold accumulated by the frozen eutectic liquid in the cold storage tank 450.

As in the case of the first embodiment, this subcooling has the effect of boosting the thermodynamic efficiency and, as a result, the duration of the above-mentioned step of the second operating cycle is no longer the same as the duration $T_I$ of the corresponding step of the first cycle, but rather $T_{II} < T_I$. All of the subsequent specified test cycles will then take place in the same manner and mode as the second cycle. Accordingly, the advantages deriving therefrom are practically the same as the ones that have already been indicated hereinbefore in connection with the first embodiment of the present invention.

Even in the second embodiment of the present invention, should the condition occur, in which the cold storage in the tank 450 has been fully completed, i.e. the eutectic liquid has been duly frozen, the by-pass of the circuit 400 is activated. The PLC 325 will then make sure that the state of the solenoid valves in the circuit is as indicated in Table 8 below:

TABLE 8

| $I^A = 408$ | $II^A = 442$ | $III^A = 443$ | $IV^A = 456$ | $V^A = 462$ |
|---|---|---|---|---|
| ON | OFF | ON | OFF | ON |

Although the invention has been described above with particular reference to a couple of preferred embodiment thereof, it will be appreciated that the invention itself may be implemented also in a number of different forms and variants without departing from the scope thereof as defined by the appended claims.

The invention claimed is:

1. Climatic test chamber, in which during a sequence of specified test cycles at least one test cavity is cooled down to and maintained at a minimum set temperature by a refrigerating unit including at least a refrigerating circuit where a refrigerant medium flows therethrough, comprising:
   a compressor, with a delivery pipe and a suction pipe, driven by an electric motor, whose rotating speed is adjustable between a maximum value and a minimum value,
   a condenser,
   an evaporator having an inlet and an outlet,
   a throttling device located at the end of a main pipe, between the condenser and the inlet of the evaporator,
   a tank which is filled with a cold storage medium and through which there are caused to pass:
      a secondary pipe extending between a first and a second fitting along said main pipe, upstream of said throttling device,
      a recovery pipe extending between a third fitting downstream of said second fitting along said main pipe and a fourth fitting along said suction pipe;
   means for selectively controlling the flow of the refrigerant medium through the main pipe, the secondary pipe, and the recovery pipe so as:
      to have cold storage medium cooled by the refrigerant medium flowing through said secondary pipe during the steps of the test cycles in which said test cavity is maintained at the minimum set temperature, said steps being carried out with the drive motor of the compressor operating at the minimum rotating speed thereof, and
      to recover the cold accumulated by the cold storage medium, by subcooling the refrigerant medium flowing through said secondary pipe during the cooling-down steps of the test cycles, said steps being carried out with the drive motor of the compressor operating at the maximum rotating speed thereof.

2. Climatic test chamber according to claim 1, wherein said refrigerating circuit forms the higher-temperature stage of a two-stage cascade refrigerating unit, in which said evaporator forms the cold side of a heat exchanger having as the hot side thereof the condenser of a second refrigerating circuit that forms the lower-temperature stage of the same refrigerating unit, and where the evaporator of said second refrigerating circuit is in a heat-exchange relation with said at least one test cavity.

3. Climatic test chamber according to claim 1, wherein said compressor is driven by the electric motor, the rotating speed of which is controlled by means of an inverter.

4. Climatic test chamber according to claim 1, characterized by the provision of a programmable control unit.

5. Climatic test chamber according to claim 1, wherein said cold storage medium is a eutectic liquid.

6. Climatic test chamber according to claim 1, wherein said cold storage medium is an aqueous ethylene glycol solution.

7. Climatic test chamber according to claim 1, wherein the compressor is driven by an asynchronous motor.

8. Climatic test chamber according to claim 1, wherein heating elements are installed in a heat-exchange relation with said at least one test cavity.

9. Method for carrying out a sequence of planned test cycles in a climatic test chamber comprising the steps of cooling down at least one test cavity and maintaining it at a minimum set temperature by means of a refrigerating unit, the refrigerating unit comprising at least one refrigerating circuit where a refrigerant medium flows therethrough, and a compressor whose rotating speed is adjustable between a maximum value and a minimum value, wherein during said steps in which said cavity is maintained at said minimum set temperature, the compressor operates at the minimum rotating speed thereof and the refrigeration capacity is used to cool a cold storage medium and store energy within, while during the cooling-down steps in which the compressor operates at the maximum rotating speed thereof, the energy stored by said cold storage medium is recovered to subcool the refrigerant medium in said refrigerating circuit.

10. A climatic test chamber system comprising:
   a compressor;
   a condenser;
   an evaporator;
   a tank configured to be filled with a cold storage medium;
   a main pipe positioned between an outlet of the compressor and an inlet of the evaporator;
   a secondary pipe separate from the main pipe, wherein the secondary pipe is positioned between the outlet of the compressor and the inlet of the evaporator, and the secondary pipe passes through the tank;
   a return pipe extending between an outlet of the evaporator and an inlet of the compressor;
   a recovery pipe extending between the return pipe and the main pipe, wherein the recovery pipe passes through the tank; and
   means for selectively controlling the flow of the refrigerant medium through the main pipe, the secondary pipe, the return pipe, and the recovery pipe so as:
      during a first cool-down cycle, fluid circulates from the outlet of the compressor, through the main pipe, to the inlet of the evaporator, and back to the inlet of the compressor through the return pipe;
      during a temperature maintenance cycle, fluid circulates from the outlet of the compressor, through the main pipe, to the inlet of the evaporator, and both back to the inlet of the compressor through the return pipe, and to the main pipe through the recovery pipe and the tank; and during a second cool-down cycle, fluid circulates from the outlet of the compressor, through the secondary pipe and the tank, to the inlet of the evaporator, and both back to the inlet of the compressor through the return pipe, and to the main pipe through the recovery pipe and the tank.

11. The system of claim 10, wherein means for selectively controlling the flow of the refrigerant medium through the main pipe, the secondary pipe, the return pipe and the recovery pipe include a first valve located along the main pipe upstream of the evaporator, a second valve located along the secondary pipe upstream of the tank, and a third valve located along the recovery pipe downstream of the tank.

12. The system of claim 10, further comprising an electric motor configured to drive the compressor, wherein the electric motor is configured to rotate at speeds adjustable between a maximum valve and a minimum value.

13. The system of claim 12, wherein during the first cool-down cycle the electric motor is configured to rotate at the maximum value speed, and during the temperature maintenance cycle the electric motor is configured to rotate at the minimum value speed.

14. The system of claim 12, further comprising an inverter, wherein the inverter is configured to control a rotating speed of the motor.

15. The system of claim 10, wherein the compressor, the condenser, the evaporator, the tank, the main pipe, the secondary pipe, the return pipe, the recovery pipe, and the means for selectively controlling the flow of the refrigerant medium define a higher-temperature stage of a two-stage cascade refrigerating unit, the evaporator forming a cold side of a heat exchanger with a lower-temperature stage forming the hot side of the heat exchanger.

16. The system of claim 10, wherein the tank is filled with an aqueous ethylene glycol solution.

17. The system of claim 10, wherein the tank is filled with a eutectic liquid.

* * * * *